US009204623B2

(12) United States Patent
Bayer et al.

(10) Patent No.: US 9,204,623 B2
(45) Date of Patent: Dec. 8, 2015

(54) TRANSGENIC MOUSE MODEL EXPRESSING AMYLOID β 4-42 PEPTIDE

(75) Inventors: Thomas Bayer, Gottingen (DE); Oliver Wirths, Friedland (DE)

(73) Assignee: GEORG-AUGUST-UNIVERSITÄT GÖTTINGEN STIFTUNG ÖFFENTLICHEN RECHTS, UNIVERSITÄTSMEDIZIN, Gottingen (DE)

( * ) Notice: Subject to any disclaimer, the term of this patent is extended or adjusted under 35 U.S.C. 154(b) by 413 days.

(21) Appl. No.: 13/702,390

(22) PCT Filed: Jun. 8, 2010

(86) PCT No.: PCT/EP2010/058024
§ 371 (c)(1),
(2), (4) Date: Mar. 27, 2013

(87) PCT Pub. No.: WO2011/154037
PCT Pub. Date: Dec. 15, 2011

(65) Prior Publication Data
US 2013/0179998 A1 Jul. 11, 2013

(51) Int. Cl.
A01K 67/00 (2006.01)
G01N 33/00 (2006.01)
A01K 67/027 (2006.01)
C07K 14/47 (2006.01)
C12N 15/85 (2006.01)

(52) U.S. Cl.
CPC ......... *A01K 67/0278* (2013.01); *A01K 67/0275* (2013.01); *C07K 14/4711* (2013.01); *A01K 2217/052* (2013.01); *A01K 2227/105* (2013.01); *A01K 2267/0312* (2013.01); *C12N 15/8509* (2013.01)

(58) Field of Classification Search
CPC ................... A01K 67/0275; A01K 2217/052; A01K 2267/0312
See application file for complete search history.

(56) References Cited

U.S. PATENT DOCUMENTS

2001/0044937 A1* 11/2001 Schatten et al. ................ 800/21
2009/0098052 A1 4/2009 Schilling et al.

FOREIGN PATENT DOCUMENTS

WO 2004013172 A2 2/2004
WO 2009034158 A2 3/2009
WO 2010005858 A1 1/2010

OTHER PUBLICATIONS

Hwang et al. Exp Neurol 186:20-32, 2004.*
Naito et al. J Reprod Fert 113:137-143, 1998.*
Raina et al. Gene 96-100, 2015.*
Haruyama et al. Curr Protoc Cel Biol. Mar. 2009. Chapter Unit-19. 10. doi:10.1002/0471143030.cb11910s42.*
Bayer et al. "Alzheimer's Disease. Molecular Pathology, Animal Models, and Current Treatment". Der Nervenarzt Suppl 3. pp. 117-127. 2008.
Bayer et al. "Dietary Cu Stabilized Brain Superoxide Dismutase 1 Activity and Reduces Amyloid Aβ Production in APP23 Transgenic Mice". PNAS. vol. 100, No. 24, pp. 14187-14192. Nov. 25, 2003.
Bayer et al. "Intracellular Accumulation of Amyloid-Beta—A Predictor for Synaptic Dysfunction and Neuron Loss in Alzheimer's Disease". Frontiers in Aging Neuroscience. vol. 2, pp. 1-10. Mar. 10, 2010.
Bayer et al. "Review on the APP/PS1Kl Mouse Model" Intraneuronal Aβ Accumulation Triggers Axonopathy, Neuron Loss and Working Memory Impairment. Genes, Brain, and Behavior. vol. 7 (Suppl. 1) pp. 6-11 2008.
Breyhan et al. "APP/PS1Kl Bigenic Mice Develop Early Synaptic Deficits and Hippocampus Atrophy". Acta Neuropathol. vol. 117, pp. 677-685. Apr. 2009.
Burright et al. "SCA1 Transgenic Mice: A Model for Neurodegeneration Cause by an Expanded GAG Trinucleotide Repeat". Cell, vol. 82, pp. 937-948. Sep. 22, 1995.
Cai et al. "BACE1 is the Major β-Secretase for Generation of Aβ Peptides by Neurons". Nature Neuroscience. vol. 4, No. 3, pp. 233-234. Mar. 2001.
Caroni et al. "Overexpression of Growth-Associated Proteins in the Neurons of Adult Transgenic Mice". Journal of Neuroscience Methods. vol. 71, pp. 3-9. 1997.
Casas et al. Massive CA1/2 Neuronal Loss myth Intraneuronal and N-terminal Truncated Aβ42 Accumulation in a Novel Alzheimer Transgenic Model. American Journal of Pathology. vol. 165, No. 4. Oct. 2004.
Christensen et al. "Intracellular Aβ Triggers Neuron Loss in the Cholinergic System of the APP/PS1Kl Mouse Model of Alzheimers Disease". Neurobiology of Aging. vol. 31, pp. 1153-1163. 2010.
Cynis et al. "Inhibition of Glutaminyl Cyclase Alters Pyroglutamate Formation in Mammalian Cells". Biochimicha et Biophysica Acta vol. 1764, pp. 1618-1625. 2006.
Demeester et al. "Comparison of the Aggregation Properties, Secondary Structure and Apoptotic Effects of Wild-Type, Flemish and Dutch N-Terminally Truncated Amyloid β-Peptides". European Journal of Neuroscience, vol. 13, pp. 2015-2024. 2001.
Holcomb et al. "Behavioral Changes in Transgenic Mice Expressing Both Amyloid Precursor Protein and Presenilin-1 Mutations: Lack of Association with Amyloid Deposits". Behavior Genetics, vol. 29, No. 3, pp. 177-185. 1999.
Kuo et al. "Compantive Analysis of Amyloid-β Chemical Structure and Amyloid Plague Morphology of Transgenic Mouse and Alzheimer's Disease Brains", The Journal of Biological Chemistry. vol. 276, No. 16, pp. 12991-12998, Apr. 20, 2001.
Lee et al. "Secretion and Intracellular Generation of Truncated Aβ in β-Site Amyloid-β Precursor Protein-Cleaving Enzyme Expressing Human Neurons". The Journal of Biological Chemistry. vol. 278, No. 7, pp. 4458-4466. Feb. 14, 2003.

(Continued)

Primary Examiner — Marcia S Noble
(74) Attorney, Agent, or Firm — Lando & Anastasi, LLP

(57) ABSTRACT

The present invention describes a novel transgenic mouse model for the common sporadic form of Alzheimer's disease. More particularly, the invention relates to a nucleotide sequence encoding Aβ 4-42 in functional linkage with at least a promoter, signal peptide sequence and a polyadenylation signal sequence, a cell and a transgenic non-human animal comprising said nucleotide sequence, and their respective use in screening methods.

10 Claims, 4 Drawing Sheets

(56) References Cited

OTHER PUBLICATIONS

Lewis et al. "Quantification of Alzheimer Pathology in Ageing and Dementia: Age-Related Accumulation of Amyloid-β (42) Peptide in Vascular Dementia", Neuropathology and Applied Neurobiology. vol. 32, pp. 103-118. 2006.

Liu et al. "Characterization of Aβ11-40/42 Peptide Deposition in Alzheimer's Disease and Young Down's Syndrome Brains: Implication of N-Terminally Truncated Aβ Species in the Pathogenesis of Alzheimer's Disease". Acta Neuropathol. vol. 112, pp. 163-174. 2006.

Masters et al. "Amyloid Plaque Core Protein in Alzheimer Disease and Down Syndrome". Proc. Natl. Acad. Sci. vol. 28, pp. 4245-4249. Jun. 1985.

Masters et al. "Neuronal Origin of a Cerebral Amyloid: Neurofibrillary Tangles of Alzheimer's Disease Contain the Same Protein as the Amyloid of Plaque Cores and Blood Vessels". The EMBO Journal. vol. 4, No. 11, pp. 2757-2763. 1985.

Mori et al. "Intraneuronal Aβ42 Accumulation in Down Syndrome Brain". Amyloid: J. Protein Folding Disord. vol. 9, pp. 88-102. 2002.

Pfaffl et al. "Relative Expression Software Tool (REST©) for Group-Wise Comparison and Statistical Analysis of Relative Expression Results in Real-Time PCR". Nucleic Acids Research. vol. 30, No. 9. 2002.

Piccini et al. "β-Amyloid is Different in Normal Aging and in Alzheimer Disease". The Journal of Biological Chemistry. vol. 280, No. 40, pp. 34186-34192. Oct. 7, 2005.

Portelius et al. "Mass Spectrometric Characterization of Brain Amyloid Beta Isoform Signatures in Familial and Sporadic Aizheimer's Disease". Acta Neuropathol, Apr. 24, 2010.

Schmitz et al. "Hippocampal Neuron Loss Exceeds Amyloid Plaque Load in a Transgenic Mouse Model of Alzheimer's Disease", American Journal of Pathology. vol. 164, No. 4, Apr. 2004.

Takeda et al. "Amino-Truncated Amyloid β-Peptide (Aβ5-40/42) Produced From Caspase-Cleaved Amyloid Precursor Protein is Deposited in Alzheimer's Disease Brain" The FASEB Journal. vol. 18. Nov. 2004.

Wirths et al. "A Modified β-Amyloid Hypothesis: Intraneuronal Accumulation of the β-Amyloid Peptide—The First Step of a Fatal Cascade" Journal of Neurochemistry. vol. 91, pp. 513-520. 2004.

Wirths et al, "Age-Dependent Axonal Degeneration in an Alzheimer Mouse Model". Neurobiology of Aging, vol. 28, pp. 1689-1699. 2007.

Wirths et al. "Deficits in Working Memory and Motor Performance in the APP/PS1kl Mouse Model for Alzheimer's Diease", Neurobiology of Aging, vol. 29, pp. 891-901. 2008.

Wirths et al. "Inflammatory Changes are Tightly Associated with Neurodegeneration in the Brain and Spinal Cord of the APP/PS1Kl Mouse Model of Alzheimer's Disease". Neurobiology of Aging. vol. 31, pp. 747-757. 2010.

Wirths et al. "Intraneuronal Pyroglutamate-Abeta 3-42 Triggers Neurodegeneration and Lethal Neurological Deficits in a Transgenic Mouse Model". Acta Neuropathol. vol. 118. pp. 487-496. 2009.

Wisniewski et al. "Murine Models of Alzheimer's Disease and Their Use in Developing Immunotherapies"Biochimica et Biophysica Acta. vol. 1802, pp. 847-859. 2010.

Yamamoto et al. "A Comparitive Study of Modified Bielschowsky Bodian and Thioflavin S Stains on Alzheimer's Neurofibrillary Tangles". Neuropathology and Applied Neurobiology, vol. 12, pp. 3-9. 1986.

* cited by examiner

SEQUENCE LISTING

```
<160> NUMBER OF SEQ ID NOS: 1

<210> SEQ ID NO 1
<211> LENGTH: 39
<212> TYPE: PRT
<213> ORGANISM: Homo sapiens

<400> SEQUENCE: 1

Phe Arg His Asp Ser Gly Tyr Glu Val His His Gln Lys Leu Val Phe
1               5                   10                  15

Phe Ala Glu Asp Val Gly Ser Asn Lys Gly Ala Ile Ile Gly Leu Met
                20                  25                  30

Val Gly Gly Val Val Ile Ala
            35
```

TRANSGENIC MOUSE MODEL EXPRESSING AMYLOID β 4-42 PEPTIDE

The present invention describes a novel transgenic mouse model for the common sporadic form of Alzheimer's disease. More particularly, the invention relates to a nucleotide sequence encoding Aβ 4-42 in functional linkage with at least a promoter, signal peptide sequence and a polyadenylation signal sequence, a cell and a transgenic non-human animal comprising said nucleotide sequence, and their respective use in screening methods.

BACKGROUND OF THE INVENTION

Alzheimer disease (AD) is a progressive neurodegenerative disorder characterized by the presence of extracellular amyloid plaques composed of amyloid-β (Aβ) surrounded by dystrophic neurites and neurofibrillary tangles. The discovery that certain early-onset familial forms of AD may be caused by an enhanced production of Aβ peptides have led to the hypothesis that amyloidogenic Aβ is intimately involved in the AD pathogenic process.

The generation of Aβ peptides is due to enzymatic cleavage of the larger amyloid precursor protein (APP), which represents a type I membrane protein with a large N-terminal ectodomain and a short intracellular C-terminal domain. Alternative splicing of APP yields eight isoforms with lengths of 677-770 amino acid residues, of which APP695 is the primary transcript in neurons. APP can be processed by two different pathways: (i) nonamyloidogenic processing: Cleavage by α-secretase within the Aβ domain releases a secreted form of APP (sAPPα), thereby precluding the generation of toxic Aβ peptides. Different members of the ADAM protein family (a disintegrin and metalloprotease) have been demonstrated to possess α-secretase activity. (ii) Amyloidogenic processing: This APP processing pathway results in cleavage at the β-secretase site, liberating also a secreted form of APP (sAPPβ), and leading to the generation of a membrane-associated C-terminal fragment named C99. The β-site APP cleaving enzyme 1 (BACE) belongs to the family of aspartyl proteases. Subsequent cleavage of C99 by γ-secretase activity results in the generation of 40-42 residue Aβ peptides, as well as a short intracellular APP fragment named AICD. It has been shown that γ-secretase consists of a complex of different proteins including presenilin-1 (PS1) or presenilin-2 (PS2), as well as nicastrin, anterior pharynx defective (APH-1) and presenilin enhancer 2 (PEN-2).

Mutations in either APP or in the presenilin genes have been linked to familiar, early onset forms of AD (FAD). These cases represent only a minor portion (~5%), whereas the vast majority of AD cases develop sporadically (sporadic form of AD). Most of the reported APP mutations are located near the secretase cleavage sites and lead to an overproduction of Aβ peptides. Some of these mutations (e.g. the Austrian mutation T714I) as well as a couple of PS1 mutations have a drastic effect on the Aβ42/Aβ40 ratio by strongly increasing Aβ42 production with concomitant suppression of β40 secretion.

Aβ accumulation has an important function in the etiology of AD with its typical clinical symptoms, like memory impairment and changes in personality. Even though it has been observed that Aβ localizes predominantly to abnormal endosomes, multivesicular bodies and within pre- and postsynaptic compartments, the mode of this toxic activity is still a matter of scientific debate.

A promising experimental approach to unravel the role of Aβ in AD pathology has been the generation of transgenic mice overexpressing the amyloid precursor protein (APP). All mouse models mimic the typical AD-like pathological deficits in synaptic transmission, changes in behaviour, differential glutamate responses and deficits in long-term potentiation. In addition, learning deficits and reduced brain volume were evident in transgenic APP models. These characteristics are generally attributed to the overexpression of full-length amyloid precursor protein (APP). Although learning deficits were evident in various APP models, the extent of Aβ-amyloid deposition did not correlate with the behavioural phenotype (Holcomb, L. A., et al. (1999) *Behav Genet.* 29, 177-185; Wirths, O., et al. (2008) *Neurobiology of Aging* 29, 891-901). These deficits occurred well before plaque deposition became prominent and may therefore reflect early pathological changes, likely induced by intraneuronal APP/Aβ mistrafficking or intraneuronal Aβ accumulation (reviewed in Bayer, T. A., and Wirths, O. (2008) *Genes Brain Behav* 7 Suppl 1, 6-11).

N-terminal deletions in general enhance aggregation of β-amyloid peptides in vitro. For example, Kuo et al ((2001) *J Biol Chem* 276, 12991-12998) have used an integrated chemical and morphological comparison of the Aβ peptides and amyloid plaques present in the brains of APP23 transgenic mice and human AD patients. The lack of posttranslational modifications such as N-terminal degradation, isomerization, racemization, and pyroglutamyl formation of Aβ in APP23 mice provides an explanation for the differences in solubility of Aβ from human AD and transgenic mouse plaques.

Besides Aβ peptides starting with an aspartate at position 1, a variety of different N-truncated Aβ peptides have been identified in AD brains. Ragged peptides including those beginning with phenylalanine at position 4 of Aβ have been reported as early as 1985 by Masters et al. (*Proc Natl Acad Sci USA* 82, 4245-4249). In addition, other N-terminal truncated peptides have been identified like $A\beta_{5-40/42}$ (Takeda, K., et al. (2004) *Faseb J* 18, 1755-1757), $A\beta_{11-40/42}$ (Liu, K., et al. (2006) *Acta Neuropathol (Berl)*. 112, 163-174; Lee, E. B., et al. (2003) *J Biol Chem* 278, 4458-4466), and Flemish and Dutch N-terminally truncated amyloid beta peptides (Demeester, N., et al. (2001) *Eur J Neurosci* 13, 2015-2024). Although $A\beta_{11-40/42}$ peptides have been observed in neuronal cultures and in the brains of patients with AD, the involvement of these peptides in its pathogenesis remains elusive (Cai, H., et al. (2001) *Nat Neurosci* 4, 233-234).

Moreover, N-truncated $A\beta_{3(pE)}$ peptides have been identified by several groups from AD brains (Kuo et al., supra), and a new mouse model was generated (TBA2) expressing only N-truncated $A\beta_{pE3}$ in neurons (Wirths, O, et al. (2009) *Acta Neuropathol* 118, :487-96). The TBA2 mice have a glutamate to glutamine substitution at position 3 of Aβ, which is prone to form $A\beta_{pE3}$. $A\beta_{3(pE)}$ has a higher aggregation propensity, and stability, and shows an increased toxicity compared to full-length Aβ. This model demonstrated that this peptide is neurotoxic in vivo inducing neuron loss and an associated neurological phenotype. Similarly, US 2009/0098052 A1 and WO 2009/034158 disclose transgenic mice, wherein the transgene encodes various mutant Aβ 3-40 and Aβ 3-42 peptides.

It was demonstrated that in another transgenic mouse model (Tg2576), Aβ peptides lacked a pronounced N-terminal degradation, posttranslational modifications, and cross-linkages that were frequently observed in the compact Aβ peptide deposits found in AD brain. Thus, under in vivo conditions, truncated Aβ molecules appeared to be generated by hydrolysis at multiple sites rather than by post-mortem N-terminal degradation.

Moreover, it was shown that the APP/PS1KI mouse model develops severe learning deficits at six months of age correlating with a CA1 neuron loss and an atrophy of the hippocampus (Casas, C et al. (2004) *Am J Pathol* 165, 1289-1300; Breyhan, H., et al. (2009) *Acta Neuropathol* 117, 677-685), together with a drastic reduction of long-term potentiation and disrupted paired pulse facilitation, coinciding with intraneuronal aggregation of N-terminal modified Aβ variants (Breyhan, H., (2009) *Acta Neuropathol* 117, 677-685). Notably, the APP/PS1KI mouse model exhibits a large heterogeneity of N-truncated $Aβ_{x-42}$ variants (Casas et al., supra). This was accompanied by reduced levels of pre- and post-synaptic markers.

In addition, the inventors have reported that intraneuronal Aβ rather than extracellular plaque pathology correlates with neuron loss in the hippocampus, the frontal cortex and the cholinergic system of APP/PS1KI mice expressing transgenic human mutant APP751 including the Swedish and London mutations on a murine knock-in (KI) Presenilin 1 (PS1) background with two FAD-linked mutations ($PS1_{M233T}$ and $PS1_{L235P}$).

By using mouse models expressing full-length APP, and after cleavage also C-terminal fragments and Aβ peptides, it is difficult to decipher the pathological function of specific Aβ peptides. In addition, all transgenic lines harbour mutations either from AD families (for example the APP/PS1KI or the 5×FAD mice) or an artificial one as in the TBA2 mice.

All previously reported mouse models with synaptic dysfunction, neuron degeneration and behavioural deficits are based on transgenic constructs with artificial mutations or from inherited familial AD cases. In other words, existing models are based on autosomal dominant mutations in APP and the presenilin genes, which represent models for the rare familial AD (FAD) forms only. Accordingly, there is still a need for a model for the common sporadic form of AD.

SUMMARY OF THE INVENTION

In a first aspect, the invention relates to a nucleic acid molecule comprising a nucleotide sequence, encoding a protein consisting of the amino acid sequence shown in SEQ ID NO: 1 (Aβ 4-42), in functional linkage with at least a promoter, signal peptide sequence and a polyadenylation signal sequence.

In a second aspect, the invention relates to a cell comprising the nucleic acid molecule according to the first aspect.

Further, in a third aspect, the invention pertains to a transgenic non-human animal, comprising the nucleic acid molecule according to the first aspect and/or the cell according to the second aspect.

Furthermore, in another aspect, the invention is directed to a use of the cell according to the second aspect or the transgenic non-human animal according to the third aspect in a method of identifying a candidate substance for the treatment of AD, in particular the sporadic form of AD.

In this context, still another aspect of the invention is directed to a method of identifying a candidate substance for the treatment of AD, the method comprising:
(a) providing a transgenic non-human animal according to the third aspect;
(b) administering a test substance to the non-human animal; and
(c) comparing the result of a suitable test selected from the group consisting of tests for motor coordination, neurodegeneration, synaptic transmission, behavior, differential glutamate response, long-term potentiation, learning, and/or brain volume for the non-human animal subjected to step (b) with the result of the same test for a corresponding non-human animal subjected to step (a), but not step (b);
wherein a difference in the result of said test for the non-human animal subjected to step (b) in comparison to the result of said test for the corresponding non-human animal subjected to step (a), but not step (b), is indicative of a candidate substance.

In a similar fashion, the inventions also relates to a method of identifying a candidate substance for the treatment of AD, the method comprising:
(a) providing a transgenic non-human animal according to the third aspect and subjecting said non-human animal to a suitable test selected from the group consisting of tests motor coordination, motor learning, synaptic loss, neuron loss, axonal degeneration, gliosis, neurodegeneration, synaptic transmission, learning and memory behavior, differential glutamate response, long-term potentiation, modification and clearance of amyloid pathology, and/or brain volume;
(b) administering a test substance to the non-human animal and subjecting the animal to the same test; and
(c) comparing the result obtained in step (b) with the result obtained in step (a);
wherein a difference in the result of said test for step (a) in comparison to step (b) is indicative of a candidate substance.

In a final aspect, the invention relates to a method of identifying a candidate substance for the treatment of AD, the method comprising:
(a) culturing a cell according to the second aspect;
(b) contacting the cell with a test candidate substance; and
(c) comparing the result of a suitable test selected from the group consisting of tests for survival or cell death, proliferation rate, and neurite extension for the cell subjected to step (b) to a corresponding cell subjected to step (a), but not step (b);
wherein a difference in the result of said test for the cell subjected to step (b) in comparison to the result of said test for the corresponding cell subjected to step (a), but not step (b), is indicative of a candidate substance.

DETAILED DESCRIPTION OF THE PREFERRED EMBODIMENTS

The inventors have recently shown that intraneuronal accumulation of Aβ peptides induces severe neuron loss and associated neurological phenotypes in diverse mouse model for Alzheimer disease (AD). Given the increasing interest in mouse models for sporadic AD, the inventors have generated four different lines of transgenic mice expressing Aβ 4-42 (TBA8 transgenic mice) under the control of the neuron specific Thy1 promoter. This is the first mouse model without any mutations showing neurological deficits. The mice accumulate abundant intraneuronal Aβ peptides in hippocampus CA1, cortical pyramidal neurons, spinal cord, pons and several subcortical nuclei. The presence of extracellular plaques proves that the peptides are secreted however the majority of Aβ peptides accumulate within neurons. Previously the inventors have demonstrated in other transgenic mouse models representing familial AD that intraneuronal accumulation of Aβ peptides are the major trigger for neuron loss and associated behavioural deficits.

In conclusion, the TBA8 model disclosed herein represents a mouse model for the common sporadic form of AD, as the neurological phenotype is due to wild type Aβ peptide aggregation. TBA8 mice harbour no mutation in the coding region of Aβ, but start with a naturally occurring N-terminal truncation of the first three amino acids of Aβ (Masters, C. L., et al. (1985) *Embo J* 4, 2757-2763; Portelius, E., et al. (2010) *Acta Neuropathol*), DOI: 10.1007/s00401-010-0690-1). Since it is known that models based on autosomal dominant mutations in APP and the presenilin genes represent only models for the rare familial AD forms, the TBA8 mice having no mutation represent a model for the common sporadic form of AD.

Accordingly, in a first aspect, the invention relates to a nucleic acid molecule comprising a nucleotide sequence, encoding a protein consisting of the amino acid sequence shown in SEQ ID NO: 1 (Aβ 4-42), in functional linkage with at least a promoter, signal peptide sequence and a polyadenylation signal sequence.

Aβ 4-42 is a peptide having the following amino acid sequence:

```
                                              (SEQ ID NO: 1)
FRHDSGYEVHHQKLVFFAEDVGSNKGAIIGLMVGGVVIA
```

Said Aβ 4-42 originates from human APP, and although it has been found in plaques of AD patients together with other Aβ peptides, its exclusive pathological role was not known. Specifically, SEQ ID NO: 1 represents an N-truncated wild-type Aβ-peptide ranging from position 4 to 42 of the human wild-type Aβ-peptide.

The nucleic acid molecule may consist of any nucleic acid capable of comprising a nucleotide sequence encoding Aβ 4-42, such as single-stranded or double-stranded DNA, the sense or antisense strand of a DNA molecule, or RNA molecules, and the like. The person skilled in the art knows how to derive a polynucleotide sequence coding for a protein and how to isolate or produce a nucleic acid sequence using standard techniques of molecular biology. Further, the nucleotide sequence may also be adapted to the codon usage of the host intended to be transfected with the nucleotide sequence.

The nucleotide sequence is in functional linkage with at least a promoter, signal peptide sequence and a polyadenylation signal sequence. However, the nucleotide sequence may be in functional linkage with further control sequences that facilitate expression of the Aβ 4-42 peptide.

The nucleic acid molecule encoding the Aβ 4-42 peptide may be included in an expression construct such as a vector, plasmid, virus/phagemid, artificial chromosome, cosmid, and further constructs known to the skilled person in order to provide for expression of the Aβ 4-42 peptide. Such an expression vector may further comprise a selectable marker, which provides for positive selection of transfected cells, i.e. transfected cells exhibit resistance to the selection and are able to grow, whereas non-transfected cells generally die. Examples of selective markers include puromycin, zeocin, neomycin (neo) and hygromycin B, which confer resistance to puromycin, zeocin, amino glycoside G-418 and hygromycin, respectively. However, other selection methods known to the skilled person may also be suitable. Moreover, such a vector or plasmid may contain elements that permit stable integration of the nucleotide sequence into a host's genome or autonomous replication of the nucleotide sequence independent of the genome.

Techniques for modifying nucleic acid sequences for insertion into a vector e.g. by utilizing recombinant DNA methods are also well-known in the art. Generally, an expression vector comprises the polynucleotide to be expressed, which is operably linked to one or more control sequences (e.g., promoter, transcriptional stop signal, translational stop signal (stop-codon), etc.) capable of directing the expression of the peptide in the desired host cell. The promoter may be any nucleic acid sequence showing transcriptional activity in the host cell of choice. The promoter can be an inducible or constitutive, general or tissue or cell specific promoter. In a preferred embodiment, the promoter is an inducible promoter.

The term "inducible promoter" relates to any promoter capable of being turned 'on' or 'off' by a regulatory compound or a certain physical stimulus. Inducible promoters are for example the lac or tac promoters, the phosphate inducible phoA promoter, or the metallothionein promoter. Further examples of inducible promoters are known to the skilled person.

In a preferred embodiment, the promoter is a tissue or cell specific promoter, more preferably a neuron-specific promoter. The terms "tissue specific" and "cell specific" are intended to mean that a majority of the peptide is expressed in the preferred cell or tissue. However, it will be understood by the skilled person that a little unintended expression will also occur in other tissues or cells. In still another embodiment, the tissue or cell specific promoter may be endogenous to the host, i.e. a promotor which naturally occurs in the host's genome. Alternatively, the promoter may be heterogenous to the host. In one preferred embodiment, the promoter is Thy-1, neuron-specific enolase (NSE) promotor, the promoter of the prion protein or of PDGF-beta, more preferably the promoter is Thy-1 or NSE, and most preferably the promoter is Thy-1. The NSE promoter is known to the skilled person from many publications in the field.

The signal peptide sequence is a nucleotide sequence that codes for an amino acid sequence linked to the N-terminal end of the Aβ 4-42 peptide in order to facilitate the expression and intracellular trafficking of the peptide. However, any signal peptide sequence is cleaved from the Aβ 4-42 peptide, thereby releasing the mature Aβ 4-42 peptide. Effective signal peptide sequences are known in the art. In a preferred embodiment, the signal peptide ist the murine pre-pro-TRH signal sequence. Another suitable signal sequence is also included in the Thy1.2 expression cassette, as described in (cf. Caroni P (1997) *J Neurosci Methods* 71(1):3-9).

A polyadenylation signal sequence is a sequence in functional linkage with the 3'terminus of the nucleotide sequence encoding the Aβ 4-42 peptide and which, when transcribed, is recognized by the host as a signal to add polyadenosine residues to the transcribed mRNA. Any polyadenylation signal sequence which is functional in the intended host may be used.

The nucleotide sequence may also contain a leader sequence, a nontranslated part of an mRNA which is important for translation by the host. The leader sequence is in functional linkage with the 5' terminus of the nucleotide sequence encoding the Aβ 4-42 peptide. Any leader sequence that is functional in the host of choice may be used.

Suitable promoters, signal peptide sequences, polyadenylation signals and other useful or necessary control sequences, and in particular the Thy-1 expression cassette, are well known in the art (cf. Caroni P (1997), supra). The selection of promoters, vectors and other elements is a matter of routine design within the level of ordinary skill in the art and many different such control sequences are described in the literature and available through commercial suppliers. Generally, the choice of the vector will typically depend on the choice of the host cell into which the vector will be introduced.

In a second aspect, the invention relates to a cell comprising the nucleic acid molecule described above.

The nucleic acid molecule, e.g., comprised in an expression vector, may be introduced into cells by various ways, e.g., using a virus as a carrier or by transfection including e.g. by chemical transfectants (such as Lipofectamine, Fugene, etc.), electroporation, calcium phosphate co-precipitation and direct diffusion of DNA. Suitable transfection techniques are known to the skilled person and the method of choice will vary depending on the host cell to be transfected. Transfection of a cell may yield stable cells or cell lines, if the transfected polynucleotide or expression vector is integrated into the genome, or by using episomal replicating plasmids, i.e. that the inheritance of the extrachromosomal plasmid is controlled by control elements that are integrated into the cell genome. In addition, unstable (transient) cells or cell lines, wherein the transfected DNA exists in an extrachromosomal form can be produced. In a preferred embodiment, the nucleic acid molecule or at least the part encoding Aβ 4-42 is introduced into the cell by pronuclear injection.

The cell may be maintained and cultured at an appropriate temperature and gas mixture (typically, 37° C., 5% $CO_2$), optionally in a cell incubator as known to the skilled person. Culture conditions may vary for each cell type, and variation of conditions for a particular cell type can result in different phenotypes. Furthermore, recipes for growth media can vary in pH, glucose concentration, growth factors and the presence of further suitable nutrient components. Growth media are commercially available, or can be prepared according to compositions, which are for example obtainable from the American Tissue Culture Collection (ATCC). Growth factors used for supplement media are often derived from animal blood such as calf serum, but also other probably cell specific growth factors may be enclosed. Additionally, antibiotics may be added to the growth media to prevent undesired microbial growth.

In general, the cell may be any kind of cell such as for example an isolated cell. For the expression and purification of the nucleotide sequence and the Aβ 4-42 peptide of the invention, a prokaryotic cell may be used, such as an *E. coli* strain. However, for other purposes, including the methods described herein, a eukaryotic cell or cell line may be used. Many cell lines which may be used in the invention are commercially available from culture collection such as the ATCC or from other commercial suppliers.

In a preferred embodiment, the cell is a vertebrate cell, preferably a mammalian cell. In a more preferred embodiment, the cell is a rodent cell, such as a mouse or a rat cell. In another more preferred embodiment, the cell is a primate cell, or a non-human embryonic stem cell, such as a fertilized oocyte. In still another preferred embodiment, the cell is an adult stem cell. In another preferred embodiment the cell may be a conventional cell used in screening processes, such as a Hela cell, Cos cell, CHO cell, or HEK cell. In a most preferred embodiment, the cell is a neuronal cell. In another most preferred embodiment, the cell is a neuroblastoma cell, such as a SY5Y or an N2a cell. It is also preferred that the cell does not comprise a nucleotide sequence encoding for a non-wt (human) APP or non-wt (human) presenilin, i.e. that the cell does not comprise a nucleotide sequence encoding APP and/or presenilin having a mutation known to be associated with familiar Alzheimer's disease (FAD). It is noted that those cells or cell lines, particularly human embryonic stem or germline cells, are excluded, which are not subject to patentability under the respective patent law or jurisdiction.

In a further aspect, the invention provides a transgenic non-human animal comprising the nucleic acid molecule and/or the cell according to the invention. The transgenic non-human animal may be any animal other than a human. In a preferred embodiment, the transgenic non-human animal is a vertebrate, preferably a mammal, more preferably a rodent, such as a mouse or a rat, or a primate.

In particular, some model organisms are preferred, such as *Caenorhabditis elegans, Arbacia punctulata, Ciona intestinalis, Drosophila,* usually the species *Drosophila melanogaster, Euprymna scolopes, Hydra, Loligo pealei, Pristionchus pacificus, Strongylocentrotus purpuratus, Symsagittifera roscoffensis,* and *Tribolium castaneum.* Among vertebrates, these are several rodent species such as guinea pig (*Cavia porcellus*), hamster, mouse (*Mus musculus*), and rat (*Rattus norvegicus*), as well as other species such as chicken (*Gallus gallus domesticus*), cat (*Felis cattus*), dog (*Canis lupus familiaris*), Lamprey, Japanese ricefish (*Oryzias latipes*), Rhesus macaque, *Sigmodon hispidus,* zebra finch (*Taeniopygia guttata*), pufferfish (*Takifugu rubripres*), african clawed frog (*Xenopus laevis*), and zebrafish (*Danio rerio*). Also preferred are non-human primates, i.e. all species of animals under the order Primates that are not a member of the genus *Homo*, for example rhesus macaque, chimpanzee, baboon, marmoset, and green monkey. However, these examples are not intended to limit the scope of the invention.

In a preferred embodiment, the transgenic non-human animal is heterozygous for the nucleic acid molecule. In another preferred embodiment, the transgenic non-human animal is homozygous for the nucleic acid molecule.

However, it is noted that those animals are excluded, which are not likely to yield in substantial medical benefit to man or animal and which are therefore not subject to patentability under the respective patent law or jurisdiction. Moreover, the skilled person will take appropriate measures, as e.g. laid down in international guidelines of animal welfare, to ensure that the substantial medical benefit to man or animal will outweigh any animal suffering.

Such a transgenic non-human animal may serve as a model system for Alzheimer's disease (AD), in particular the sporadic form of AD. However, since Aβ-peptides are linked to diseases associated with amyloidogenesis and/or amyloid-plaque formation, such as Down Syndrome, Mild Cognitive Impairment, cerebral amyloid angiopathy, dementia, Lewy body dementia, hereditary cerebral hemorrhage with amyloidosis Dutch type, Familial Danish Dementia, and Familial British Dementia, vascular dementia, motor neuropathy, Creutzfeld Jacob disease, Parkinson's disease, HIV-related dementia, ALS or neuronal disorders related to aging, it is also contemplated that the transgenic non-human animal of the invention may also be useful as a model system in said diseases.

In this context, another aspect of the invention is the use of a cell of the invention or the transgenic non-human animal according to the invention in a method of identifying a candidate substance for the treatment of AD, preferably the sporadic form of AD.

Likewise, it is also contemplated that the cell of the invention or the transgenic non-human animal according to the invention may also be used in a method of identifying a candidate substance for the treatment of Down Syndrome, Mild Cognitive Impairment, cerebral amyloid angiopathy, dementia, Lewy body dementia, hereditary cerebral hemorrhage with amyloidosis Dutch type, Familial Danish Dementia, and Familial British Dementia, motor neuropathy, Creutzfeld Jacob disease, Parkinson's disease, HIV-related dementia, ALS or neuronal disorders related to aging.

Accordingly, in still another aspect, the invention provides a method of identifying a candidate substance for the treatment of AD, preferably the sporadic form of AD, the method comprising:

(a) providing a transgenic non-human animal according to the invention;
(b) administering a test substance to the transgenic non-human animal; and
(c) comparing the result of a suitable test selected from the group consisting of tests for motor coordination, neurodegeneration, synaptic transmission, behavior, differential glutamate response, long-term potentiation, learning, and/or brain volume for the non-human animal subjected to step (b)
with the result of the same test for a corresponding non-human animal subjected to step (a), but not step (b);
wherein a difference in the result of said test for the non-human animal subjected to step (b) in comparison to the result of said test for the corresponding non-human animal subjected to step (a), but not step (b), is indicative of a candidate substance.

Similarly, the invention also provides a method of identifying a candidate substance for the treatment of AD, preferably the sporadic form of AD, the method comprising:
(d) providing a transgenic non-human animal and subjecting said non-human animal to a suitable test selected from the group consisting of tests motor coordination, motor learning, synaptic loss, neuron loss, axonal degeneration, gliosis, neurodegeneration, synaptic transmission, learning and memory behavior, differential glutamate response, long-term potentiation, modification and clearance of amyloid pathology, and/or brain volume;
(e) administering a test substance to the non-human animal and subjecting the animal to the same test; and
(f) comparing the result obtained in step (b) with the result obtained in step (a);
wherein a difference in the result of said test for step (a) in comparison to step (b) is indicative of a candidate substance.

The test substance may be provided in the form of a chemical compound library including a plurality of chemical compounds which may have been assembled from any of multiple sources. Thus, the test substance may be a chemically synthesized molecule, or a natural product, or may have been generated by combinatorial chemistry techniques. They chemical compounds may have a common particular structure or may be compounds of a particular creature such as an animal. In the context with the present invention, the test substance may comprise small molecules, proteins or peptides. In another embodiment, the test substance may comprise additional pharmaceutically acceptable compounds and/or substances, i.e. the test substance may be in the form of a pharmaceutical composition.

Tests for motor coordination, motor learning, synaptic loss, neuron loss, axonal degeneration, gliosis, neurodegeneration, synaptic transmission, learning and memory behavior, differential glutamate response, long-term potentiation, modification and clearance of amyloid pathology, and/or brain volume are well known to the person in the art. Suitable test are described, for example, in Wirths O, et al. (2007) Age-dependent axonal degeneration in an Alzheimer mouse model. *Neurobiol Aging* 28:1689-1699; Wirths O, et al. (2010) Inflammatory changes are tightly associated with neurodegeneration in the brain and spinal cord of the APP/PS1KI mouse model of Alzheimer's disease. *Neurobiol Aging* 31(5):747-757; Schmitz C, et al. (2004) Hippocampal neuron loss exceeds amyloid plaque load in a transgenic mouse model of Alzheimer's disease. *Am J Pathol* 164(4): 1495-1502; Breyhan H, et al. (2009) APP/PS1KI bigenic mice develop early synaptic deficits and hippocampus atrophy. *Acta Neuropathol* 117(6):677-685; Wirths O, et al. (2008) Deficits in working memory and motor performance in the APP/PS1ki mouse model for Alzheimer's disease. *Neurobiology of Aging* 29(6):891-901; Bayer T A, et al. (2003) Dietary Cu stabilizes brain SOD-1 activity and reduces amyoid Aβ production in APP23 transgenic mice. *PNAS* 100 (24):14187-14192. Further tests are described in Example 2 of US 2009/0098052 A1. All above documents are hereby incorporated by reference. Further tests are exemplified in the examples section below. The skilled person will know which test is suitable, depending on the choice of the transgenic non-human animal.

If the transgenic non-human animal(s) subjected to step (b) has/have an improved motor coordination, motor learning, synaptic transmission, learning and memory behavior, long-term potentiation, modification and clearance of amyloid pathology, and/or brain volume compared to the corresponding transgenic non-human animal(s) subjected to step (a), but not step (b), this is indicative for the capability of the substance to prevent or reduce AD, in particular the sporadic form of AD.

Likewise, if the transgenic non-human animal(s) subjected to step (b) has/have a decreased synaptic loss, neuron loss, axonal degeneration, gliosis, and/or neurodegeneration compared to the corresponding transgenic non-human animal(s) subjected to step (a), but not step (b), this is indicative for the capability of the substance to prevent or reduce AD, in particular the sporadic form of AD.

Finally, the invention also provides a method of identifying a candidate substance for the treatment of AD, preferably the sporadic form of AD, the method comprising:
(a) culturing a cell;
(b) contacting the cell with a test candidate substance; and
(c) comparing the result of a suitable test selected from the group consisting of tests for survival or cell death, proliferation rate, and neurite extension for the cell subjected to step (b) to a corresponding cell subjected to step (a), but not step (b);
wherein a difference in the result of said test for the cell subjected to step (b) in comparison to the result of said test for the corresponding cell subjected to step (a), but not step (b), is indicative of a candidate substance.

The proliferation rate and the survival of the cells may be determined by counting the cells. Alternatively, cell proliferation, may be determined by an XTT assay (Roche). Tests for determining the percentage of apoptotic cells are also well known in the art. For example, there are commercially available as kits, such as kits comprising a fluorescence-dye labelled anti Annexin V antibody (abcam, BD, BIOMOL). Another example for determining apoptotic cells is TUNEL (Terminal deoxynucleotidyl Transferase Biotin-dUTP Nick End Labeling). Specifically late apoptotic cells may also be detected by adding ethidium bromide to a sample of the cells following analysis. Neurite extension may be assayed by microscopic analysis. Cell death may also be measured by determining "cell death markers", such as the degradation of Aβ 4-42 and/or inhibition of Aβ 4-42. Cell death markers may be determined by transcriptomics, lipidomics, proteomics, ELISA, Western blot, Dot Blot, or histological and/or immunocytochemical staining In the context of the present invention, a proliferation rate of the cells subjected to step (a), but not step (b) of less than 70%, in particular less than 60%, less than 50%, less than 40%, less than 30%, less than 20%, less than 10%, or less than 5% in comparison to the cells which has been subjected to step (a) and (b) is indicative for an increase in the proliferation rate.

In the context of the present invention, a neurite extension of the cells subjected to step (a), but not step (b) of less than 70%, in particular less than 60%, less than 50%, less than 40%, less than 30%, less than 20%, less than 10%, or less than 5% in comparison to the cells which has been subjected to step (a) and (b) is indicative for an increase of neurite extension.

In the context of the present invention, a percentage of apoptotic cells among the cells subjected to step (a) and (b) of less than 70%, in particular less than 60%, less than 50%, less than 40%, less than 30%, less than 20%, less than 10%, or less than 5% in comparison to the cells which have been subjected to step (a), but not step (b), is indicative for a decrease in the percentage of apoptotic cells.

If the cell(s) subjected to step (a) and (b) has/have an increased proliferation rate and or neurite extension compared to the corresponding cell(s) subjected to step (a), but not step (b), this is indicative for the capability of the substance to prevent or reduce AD, in particular the sporadic form of AD.

Likewise, if the cell(s) subjected to step (a) and (b) has/have a decreased percentage of apoptotic cells compared to the corresponding cell(s) subjected to step (a), but not step (b), this is indicative for the capability of the substance to prevent or reduce AD, in particular the sporadic form of AD.

The person skilled in the art will know which assay to choose depending on the cell which is applied in the method of the invention.

EXAMPLES

Example 1

Generation of Transgenic TBA8 Founder Mice

Figure 1:
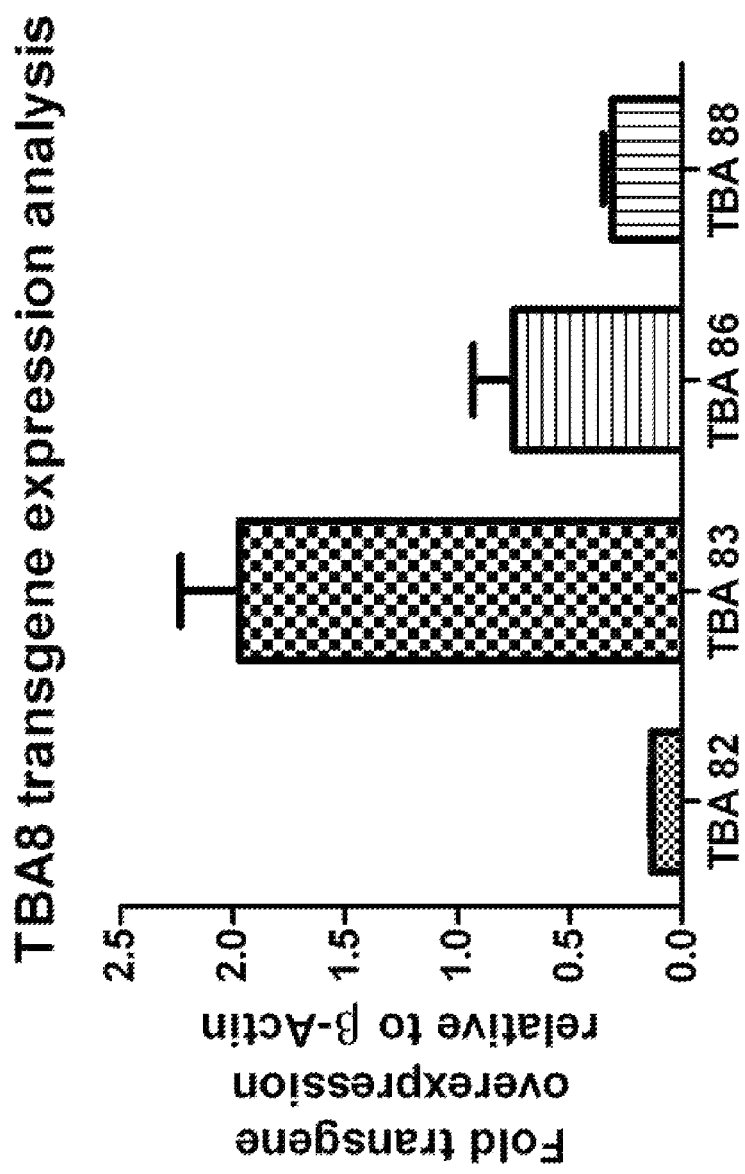
FIG. 1. RT-PCR analysis of transgene expression in different TBA8 lines. Relative expression levels of TBA8 transcript levels normalised to β-Actin (P=0.019).

The amyloid-beta peptide 4-42 was expressed as fusion protein with the pre-pro sequence of murine thyrotropin-releasing hormone (TRH), to be released by a prohormone convertase as described earlier (1). The cDNA of human wildtype APP was used to generate the sequence for Aβ 1-42 and subsequently the first nine nucleotides representing the first N-terminal three amino acids of Aβ 1-42 were deleted by site directed mutagenesis (Stratagene, QuikChange II Site-directed mutagenesis Kit Cat.-No: 200523) generating Aβ 4-42. The sequence of Aβ 4-42 was fused to the 3' end of the signal peptide of the murine TRH as described earlier (Cynis H, et al. (2006) *Biochim Biophys Acta* 1764(10):1618-1625). The respective cDNA was inserted into the pUC18 vector containing the murine Thy-1.2 sequence applying standard molecular biology techniques and verified by sequencing. The transgenic mice were generated by male pronuclear injection of fertilized C57B1/6J oocytes. The resulting offspring were further characterized for transgene integration by PCR analysis and after crossing to C57B1/6J wild type mice for transgene expression by RT-PCR. The lines with highest transgene mRNA expression were selected for further breeding (named TBA82, TBA83, TBA86, TBA88). All animals were handled according to German guidelines for animal care.

In addition to Aβ starting with aspartate at position 1 (Aβ 1-42), one major Aβ species in AD brain starts at position 4 with phenylalanine (Aβ 4-42). We generated a novel mouse model expressing Aβ 4-42 under the control of the murine Thy-1.2 promoter. Eight transgenic founder lines were obtained and crossed with C57B16 wildtype mice. Four founders giving offspring were further examined by RT-PCR in order to identify the lines with the highest expression levels.

Example 2

Determination of mRNA Levels of Different TBA8 Founders

Four transgenic founders were isolated. mRNA expression levels in brain were quantified by RT-PCR, as follows.

Total RNA was prepared using TriFast (peqlab, Germany, Cat.-Nr: 30-2010). RNA was reverse transcribed into cDNA using First Strand cDNA Synthesis Kit (Fermentas GmbH, Cat.-Nr: K1612). Quantitative real-time RT-PCR was performed using a Stratagene MX3000P Real-Time Cycler. For quantification, the DyNamo Flash SYBR Green qPCR Kit containing ROX as an internal reference dye (Finnzymes, Finland, Cat.-Nr: F-415L) was used. Specific oligonucleotide primers for TBA8 mRNA and β-actin were purchased from Eurofins MWG Operon (Germany) or Qiagen (Qiagen, Germany) respectively. Statistical analysis of quantitative real-time PCR measurements was done using the Relative Expression Software Tool V2.0.7 (REST 2008) (Pfaffl, M. W., et al. (2002) *Nucleic Acids Res.* 30, e36).

Differences between groups were tested with one-way analysis of variance (ANOVA) followed by unpaired t-tests. All data are given as means±s.e.m. Significance levels of unpaired t-tests are given as follows: *P<0.001; P<0.01; *P<0.05. Survival rate was calculated by the Logrank Test. All calculations were performed using GraphPad Prism version 4.03 for Windows (GraphPad Software, San Diego, Calif., USA).

TBA83 mice had the highest level, followed by TBA88, TBA86 and lastly TBA82. Therefore the TBA83 line was chosen for further breeding (FIG. 1).

Example 3

Phenotypic Characterization and Neuropathological Assessment of TBA83 Mice

The TBA83 transgenic mice revealed obvious macroscopic abnormalities, including growth retardation and a striking neurological phenotype characterized by loss of motor coordination (data not shown). The neurological phenotype of the TBA83 line resembles that of mouse models with neurodegeneration (for example Burright, E. N., (1995) *Cell* 82, 937-948).

Mice were anaesthetized and transcardially perfused with ice-cold phosphate-buffered saline (PBS) followed by 4% paraformaldehyde. Brain samples were carefully dissected and post-fixed in 4% phosphate-buffered formalin at 4° C.

Immunohistochemistry was performed on 4 μm paraffin sections. The following antibodies were used: 4G8 (Aβ17-24, Covance, Cat.-No: SIG-39200), GFAP (Chemicon, Cat.-No: MAB360), Iba-1 (Wako Chemicals, USA, Cat.-No: 019-19741), AT8 (Innogenetics, Belgium, Cat.-No: 90206). Biotinylated secondary anti-rabbit and anti-mouse antibodies (1:200) were purchased from Dako. Staining was visualized using the ABC method, with a Vectastain Elite ABC kit (Vector Laboratories, USA, Cat.-No: PK-6200) and diaminobenzidine as chromogen. Counterstaining was carried out with hematoxylin.

The Bielschowsky staining method was performed according to the Yamamoto and Hirano 1998 ((1986) *Neuropathol Appl Neurobiol* 12, 3-9) modification.

Figure 2:
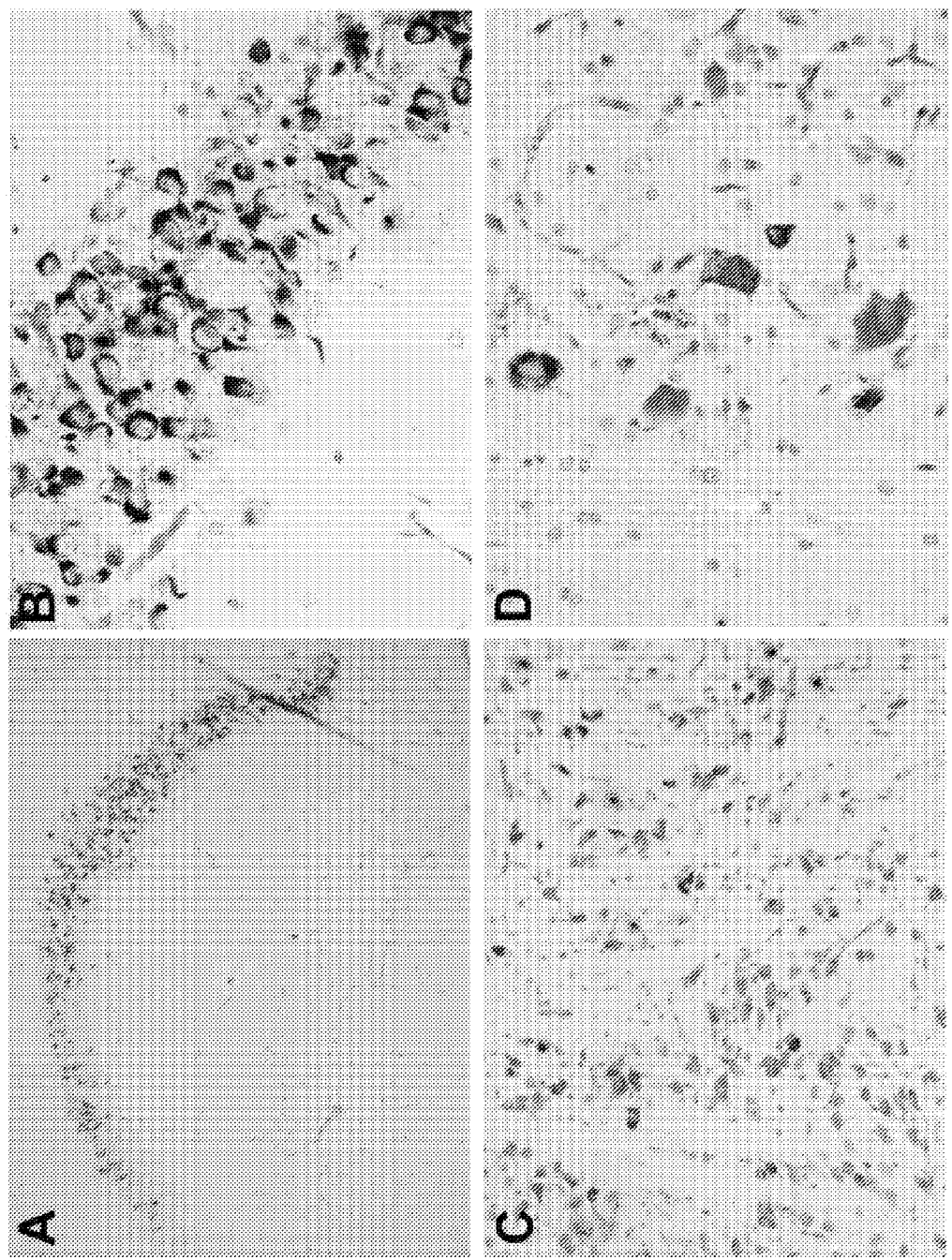
FIG. 2. Immunohistochemical staining against human Aβ (4G8) in TBA8 mouse brain at 3 months of age in the hippocampus (A, B), pons (C) and spinal cord (D).
Figure 3:
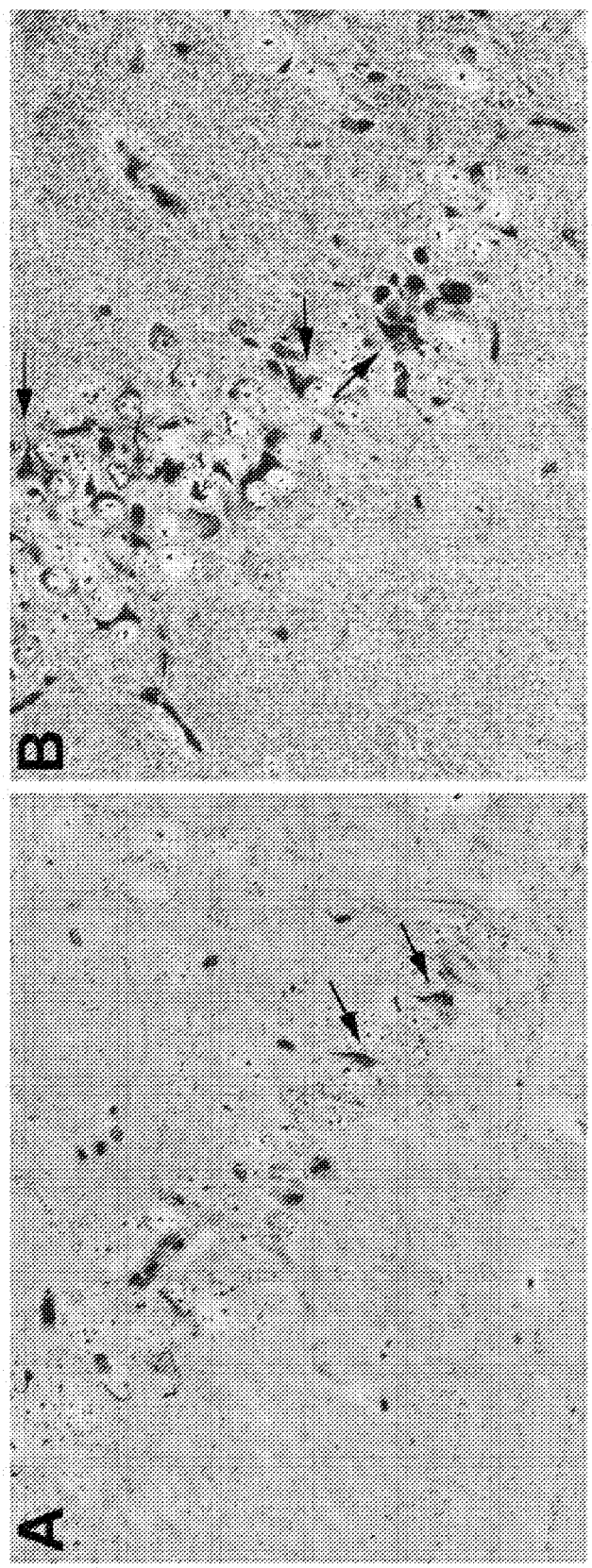
FIG. 3. Silver staining in hippocampus of a 2-month-old TBA8 mouse showing tangle-like structures in pyramidal neurons of CA1.
Figure 4:
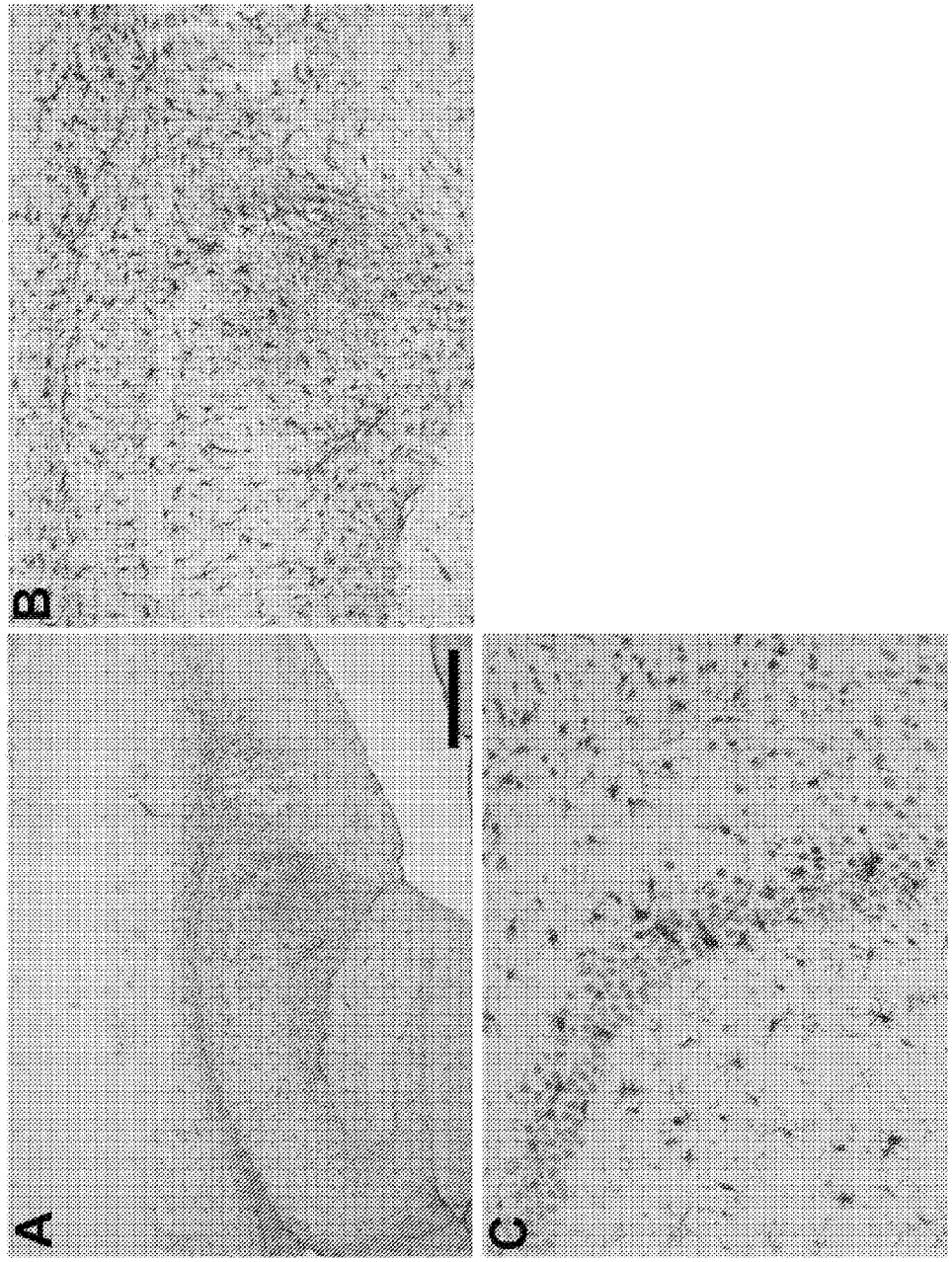
FIG. 4. Inflammatory changes in hippocampus of a 2-month-old TBA8 mouse indicating early neurodegenerative events. (A, B) GFAP staining of reactive astrocytes in hippocampus. (C) Iba1 staining of reactive microglia in hippocampus.

TBA83 brain sections showed strong immunoreactivity using antibody 4G8 against Aβ predominantly in CA1 and cortical pyramidal neurons, motor neurons in spinal cord, pons and subcortical nuclei (FIG. 2). Diffuse plaques were observed in the olfactory bulb, but were less prominent compared to intraneuronal staining. The observation of extracellular plaques demonstrates that Aβ is secreted. While no staining was obtained using an antibody against phosphorylated Tau (AT8) (not shown), pretangle like structures were demonstrated in CA1 by Bielschowski silver staining (FIG. 3). Early inflammatory reactive microglia and astroglia demonstrate hippocampal neurodegeneration (FIG. 4).

In accordance with these findings the inventors have previously shown that intraneuronal Aβ accumulation precedes plaque formation in transgenic mice expressing mutant APP695 with the Swedish, Dutch and London mutations in combination with mutant PS-1 M146L. These mice displayed abundant intraneuronal Aβ immunoreactivity in hippocampal and cortical pyramidal neurons. In young mice, a strong intraneuronal Aβ staining was detected in vesicular structures in somatodendritic and axonal compartments of pyramidal neurons and an attenuated neuronal immunoreactivity with increasing age. The intraneuronal immunoreactivity declined with increased plaque accumulation, a finding that was also reported in Down's syndrome patients, where the youngest patients displayed the strongest immunoreactivity (Mori, C., et al. (2002) *Amyloid* 9, 88-102.). The neuronal loss in CA1 of the hippocampus did not correlate with the amount of extracellular Aβ (Breyhan, H., et al. (2009) *Acta Neuropathol* 117, 677-685). The same observation has been reported in the APP/PS1M146L model (Schmitz, C., et al. (2004) *Am J Pathol* 164, 1495-1502). Hippocampal neuron loss has also been reported in the APP23 mouse model, however, whether intraneuronal Aβ contributes to the neuron loss in this model is not clear. The triple-transgenic mouse model expresses mutant APP in combination with mutant PS-1 and mutant Tau protein. These mice displayed early synaptic dysfunction before plaque or tangle deposition was evident, together with early intraneuronal Aβ immunoreactivity preceding plaque deposition. Tau and Aβ immunoreactivity co-localized in hippocampal neurons, which might imply that early intraneuronal Aβ accumulation could affect Tau pathology.

In conclusion, the TBA8 model represents a mouse model for the common sporadic form of AD, as the neurological phenotype is due to wild type Aβ peptide aggregation. TBA8 mice harbour no mutation in the coding region of Aβ, but start with a naturally occurring N-terminal truncation of the first three amino acids of Aβ. Since it is known that models based on autosomal dominant mutations in APP and the presenilin genes represent only models for the rare familial AD forms, the TBA8 mice having no mutation represent a model for the common sporadic form of AD.

LIST OF REFERENCES

US 2009/0098052 A1
WO 2009/034158

Bayer T A, et al. (2003) *PNAS* 100(24):14187-14192.

Bayer, T. A., and Wirths, O. (2008) *Genes Brain Behav* 7 Suppl 1, 6-11.

Breyhan, H., Wirths, O., Duan, K., Marcello, A., Rettig, J., and Bayer, T. A. (2009) *Acta Neuropathol* 117, 677-685.

Burright, E. N., Clark, H. B., Servadio, A., Matilla, T., Feddersen, R. M., Yunis, W. S., Duvick, L. A., Zoghbi, H. Y., and Orr, H. T. (1995) *Cell* 82, 937-948.

Cai, H., Wang, Y., McCarthy, D., Wen, H., Borchelt, D. R., Price, D. L., and Wong, P. C. (2001) *Nat Neurosci* 4, 233-234.

Caroni P (1997) *J Neurosci Methods* 71(1):3-9.

Casas, C., Sergeant, N., Itier, J. M., Blanchard, V., Wirths, O., van der Kolk, N., Vingtdeux, V., van de Steeg, E., Ret, G., Canton, T., Drobecq, H., Clark, A., Bonici, B., Delacourte, A., Benavides, J., Schmitz, C., Tremp, G., Bayer, T. A., Benoit, P., and Pradier, L. (2004) *Am J Pathol* 165, 1289-1300.

Cynis H, et al. (2006) *Biochim Biophys Acta* 1764(10):1618-1625.

Demeester, N., Mertens, C., Caster, H., Goethals, M., Vandekerckhove, J., Rosseneu, M., and Labeur, C. (2001) *Eur J Neurosci* 13, 2015-2024.

Holcomb, L. A., Gordon, M. N., Jantzen, P., Hsiao, K., Duff, K., and Morgan, D. (1999) *Behav Genet.* 29, 177-185.

Kuo, Y. M., Kokjohn, T. A., Beach, T. G., Sue, L. I., Brune, D., Lopez, J. C., Kalback, W. M., Abramowski, D., Sturchler-Pierrat, C., Staufenbiel, M., and Roher, A. E. (2001) *J Biol Chem* 276, 12991-12998.

Lee, E. B., Skovronsky, D. M., Abtahian, F., Doms, R. W., and Lee, V. M. (2003) *J Biol Chem* 278, 4458-4466.

Liu, K., Solano, I., Mann, D., Lernere, C., Mercken, M., Trojanowski, J. Q., and Lee, V. M. (2006) *Acta Neuropathol (Berl).* 112, 163-174.

Masters, C. L., Multhaup, G., Simms, G., Pottgiesser, J., Martins, R. N., and Beyreuther, K. (1985) *Embo J* 4, 2757-2763.

Masters, C. L., Simms, G., Weinman, N. A., Multhaup, G., McDonald, B. L., and Beyreuther, K. (1985) *Proc Natl Acad Sci USA* 82, 4245-4249.

Mori, C., Spooner, E. T., Wisniewsk, K. E., Wisniewski, T. M., Yamaguch, H., Saido, T. C., Tolan, D. R., Selkoe, D. J., and Lernere, C. A. (2002) *Amyloid* 9, 88-102.

Pfaffl, M. W., Horgan, G. W., and Dempfle, L. (2002) *Nucleic Acids Res.* 30, e36.

Portelius, E., Bogdanovic, N., Gustaysson, M. K., Volkmann, I., Brinkmalm, G., Zetterberg, H., Winblad, B., and Blennow, K. (2010) *Acta Neuropathol., DOI:* 10.1007/s00401-010-0690-1, Epub ahead of print)

Schmitz, C., Rutten, B. P., Pielen, A., Schafer, S., Wirths, O., Tremp, G., Czech, C., Blanchard, V., Multhaup, G., Rezaie, P., Korr, H., Steinbusch, H. W., Pradier, L., and Bayer, T. A. (2004) *Am J Pathol* 164, 1495-1502.

Takeda, K., Araki, W., Akiyama, H., and Tabira, T. (2004) *Faseb J* 18, 1755-1757.

Wirths O, Breyhan H, Cynis H, Schilling S, Demuth H-U, and TA, B. (2009) *Acta Neuropathol* 118:487-96

Wirths O, et al. (2010) *Neurobiol Aging* 31(5):747-757.

Wirths, O., Breyhan, H., Schäfer, S., Roth, C., and Bayer, T. A. (2008) *Neurobiology of Aging* 29, 891-901.

Wirths, O., Multhaup, G., and Bayer, T. A. (2004) *J Neurochem* 91, 513-520.

Wirths, O., Weis, J., Kayed, R., Saido, T. C., and Bayer, T. A. (2007) *Neurobiol Aging* 28, 1689-1699.

Yamamoto, T., and Hirano, A. (1986) *Neuropathol Appl Neurobiol* 12, 3-9.

The invention claimed is:

1. A transgenic non-human animal, comprising in its genome a heterologous nucleic acid encoding a protein consisting of the amino acid sequence shown in SEQ ID NO: 1 (Aβ 4-42) in functional linkage with at least a neuron specific promoter, a signal peptide sequence and a polyadenylation signal sequence, wherein said nucleic acid is expressed in the CA1, cortical pyramidal neurons, motor neurons of the spinal cord, pons, and subcortical nuclei in the brain of said animal, and wherein said animal develops intraneuronal amyloid plaque formation in the brain, loss of motor coordination, and neurodegeneration.

2. The transgenic non-human animal of claim 1, wherein the non-human animal is a vertebrate.

3. The transgenic non-human animal of claim 1, wherein the non-human animal is a mammal.

4. The transgenic non-human animal of claim 1, wherein the non-human animal is a rodent or a primate.

5. The transgenic non-human animal of claim 1, wherein the animal is homozygous for the nucleic acid.

6. The transgenic non-human animal of claim 1, wherein the animal is heterozygous for the nucleic acid.

7. A method of identifying a candidate substance for the treatment of Alzheimer's Disease (AD), the method comprising:
   (a) providing a transgenic non-human animal according to claim 1;
   (b) administering a test substance to the non-human animal; and
   (c) comparing the result of a suitable test selected from the group consisting of tests for motor coordination, neurodegeneration, synaptic transmission, behavior, differential glutamate response, long-term potentiation, learning, and/or brain volume for the non-human animal subjected to step (b)
      with the result of the same test for a corresponding non-human animal subjected to step (a), but not step (b);
   wherein a difference in the result of said test for the non-human animal subjected to step (b) in comparison to the result of said test for the corresponding non-human animal subjected to step (a), but not step (b), is indicative of a candidate substance for treatment of AD.

8. The method according to claim 7, wherein said AD is the sporadic form of AD.

9. A method of identifying a candidate substance for the treatment of AD, the method comprising:
   (a) providing a transgenic non-human animal according to claim 1 and subjecting said non-human animal to a suitable test selected from the group consisting of tests motor coordination, motor learning, synaptic loss, neuron loss, axonal degeneration, gliosis, neurodegeneration, synaptic transmission, learning and memory behavior, differential glutamate response, long-term potentiation, modification and clearance of amyloid pathology, and/or brain volume;
   (b) administering a test substance to the non-human animal and subjecting the animal to the same test; and
   (c) comparing the result obtained in step (b) with the result obtained in step (a);
   wherein a difference in the result of said test for step (a) in comparison to step (b) is indicative of a candidate substance for treatment of AD.

10. The method according to claim 9, wherein said AD is the sporadic form of AD.

* * * * *